(12) United States Patent
Sandhu et al.

(10) Patent No.: US 8,414,484 B2
(45) Date of Patent: Apr. 9, 2013

(54) PERCUTANEOUS TUBE ASSEMBLY

(75) Inventors: Faheem A. Sandhu, Washington, DC (US); Mahmoud F. Abdelgany, Rockaway, NJ (US); YoungHoon Oh, Montville, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 687 days.

(21) Appl. No.: 12/641,213

(22) Filed: Dec. 17, 2009

(65) Prior Publication Data

US 2011/0152624 A1 Jun. 23, 2011

(51) Int. Cl.
*A61B 1/32* (2006.01)

(52) U.S. Cl. .................................. 600/206; 600/245

(58) Field of Classification Search .............. 606/306, 606/328, 96, 99, 190–194; 600/201–218, 600/245

See application file for complete search history.

(56) References Cited

U.S. PATENT DOCUMENTS

| | | | |
|---|---|---|---|
| 2,358,867 A | 9/1944 | Madan | |
| 3,641,332 A | 2/1972 | Reick et al. | |
| 3,774,614 A | 11/1973 | Cook | |
| 4,009,382 A | 2/1977 | Nath | |
| 4,085,436 A | 4/1978 | Weiss | |
| 4,226,228 A | 10/1980 | Shin et al. | |
| 4,562,832 A | 1/1986 | Wilder et al. | |
| 4,627,421 A | 12/1986 | Symbas et al. | |
| 5,143,436 A | 9/1992 | Baylor et al. | |
| 5,159,921 A | 11/1992 | Hoover | |
| 5,448,990 A | 9/1995 | De Faria-Correa | |
| 5,520,611 A | 5/1996 | Rao et al. | |
| 5,735,792 A | 4/1998 | Vanden Hoek et al. | |
| 5,745,632 A | 4/1998 | Dreyer | |
| 5,785,648 A * | 7/1998 | Min | 600/206 |
| 5,928,139 A * | 7/1999 | Koros et al. | 600/205 |
| 6,036,328 A | 3/2000 | Ohtsuki et al. | |
| 6,080,105 A * | 6/2000 | Spears | 600/212 |
| 6,142,935 A | 11/2000 | Flom et al. | |
| 6,162,172 A | 12/2000 | Cosgrove et al. | |
| 6,176,824 B1 | 1/2001 | Davis | |
| 6,196,968 B1 | 3/2001 | Rydin et al. | |
| 6,228,025 B1 | 5/2001 | Hipps et al. | |
| 6,322,499 B1 | 11/2001 | Evans et al. | |
| 6,350,236 B1 | 2/2002 | Hipps et al. | |
| 8,206,291 B2 * | 6/2012 | Fischvogt et al. | 600/204 |
| 2001/0001260 A1 | 5/2001 | Parker et al. | |

* cited by examiner

*Primary Examiner* — Eduardo C Robert
*Assistant Examiner* — Tara Carter
(74) *Attorney, Agent, or Firm* — Rahman LLC

(57) ABSTRACT

A percutaneous tube assembly is provided for performing minimally invasive surgery, the system comprising a percutaneous tube comprising a translucent main body; an external attachment fixture attached to the main body; an access channel longitudinally bored through the main body; an internal attachment channel longitudinally bored through the main body, wherein the internal attachment channel comprises a partially smooth inner surface adjacent to a partially rough inner surface; and an internal attachment, mating with the internal attachment channel.

20 Claims, 8 Drawing Sheets

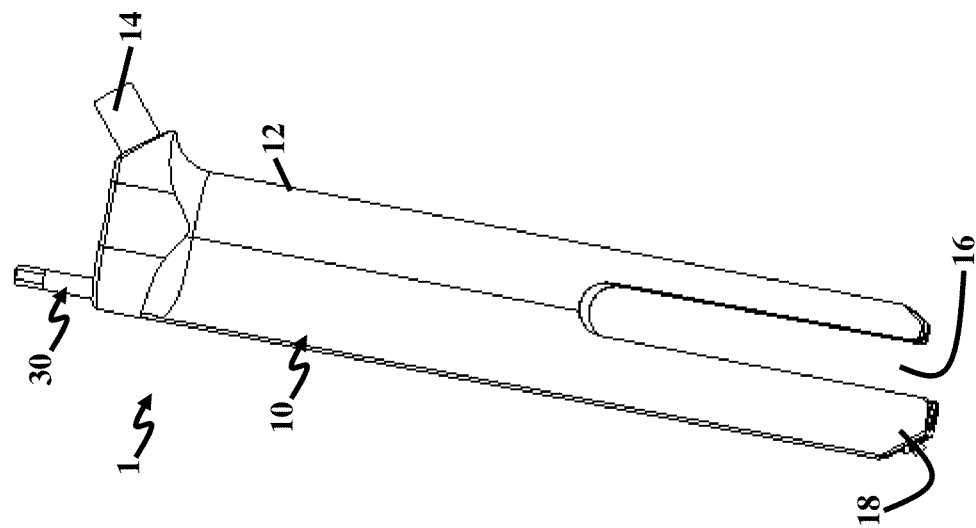

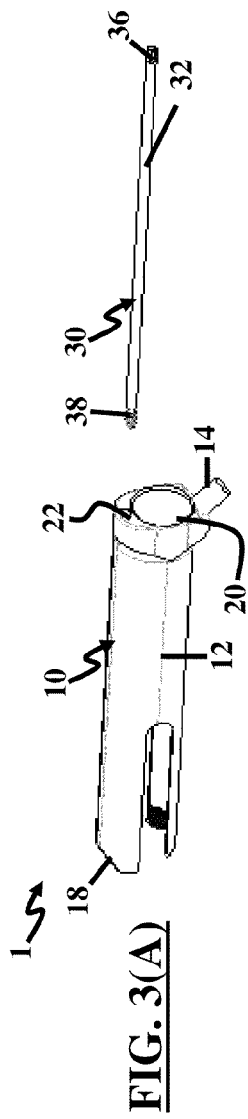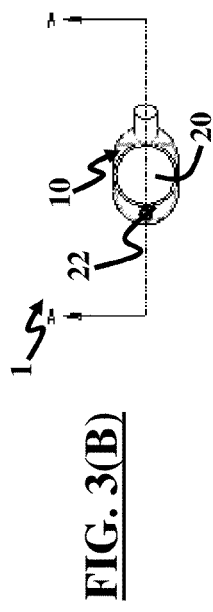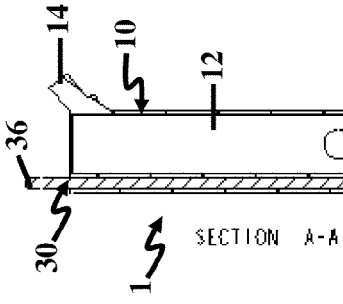
FIG. 3(A)
FIG. 3(B)
FIG. 3(C)

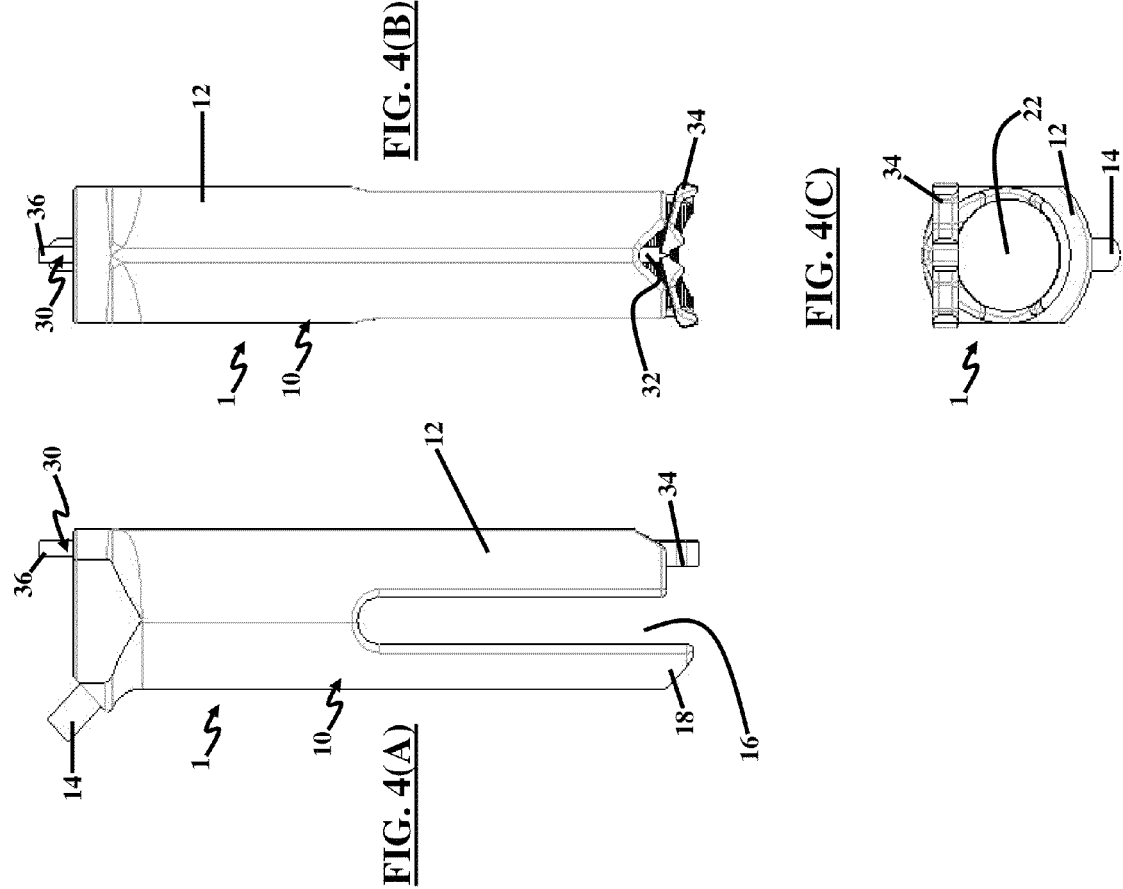

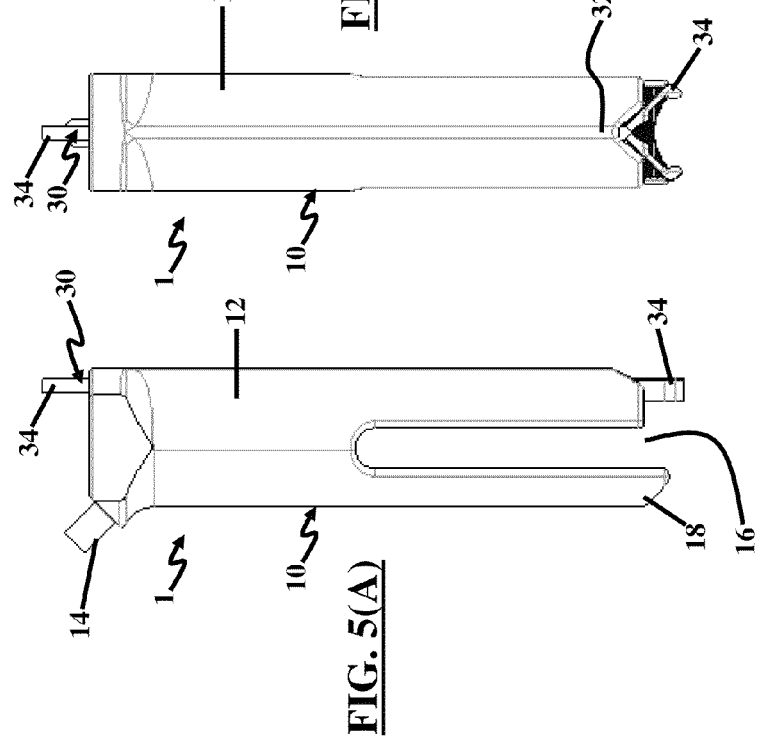
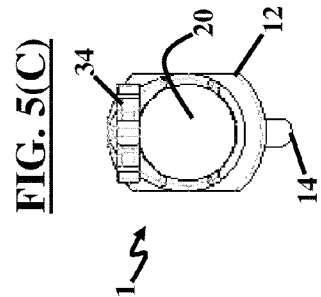
FIG. 5(A)
FIG. 5(B)
FIG. 5(C)

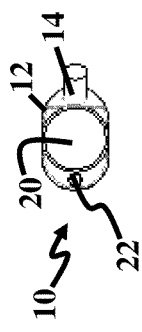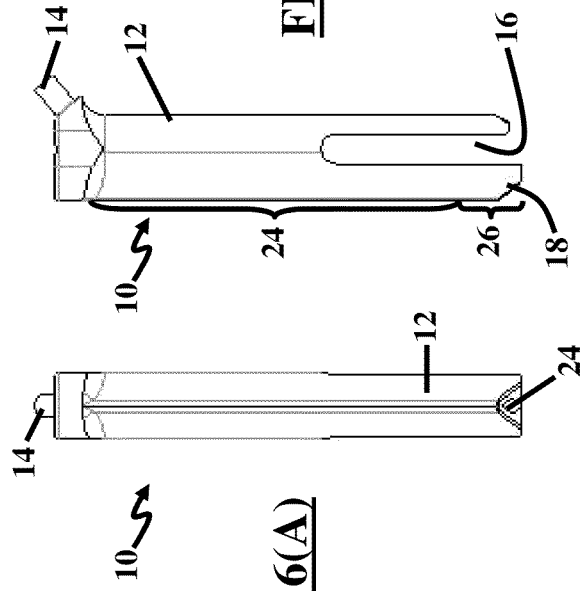

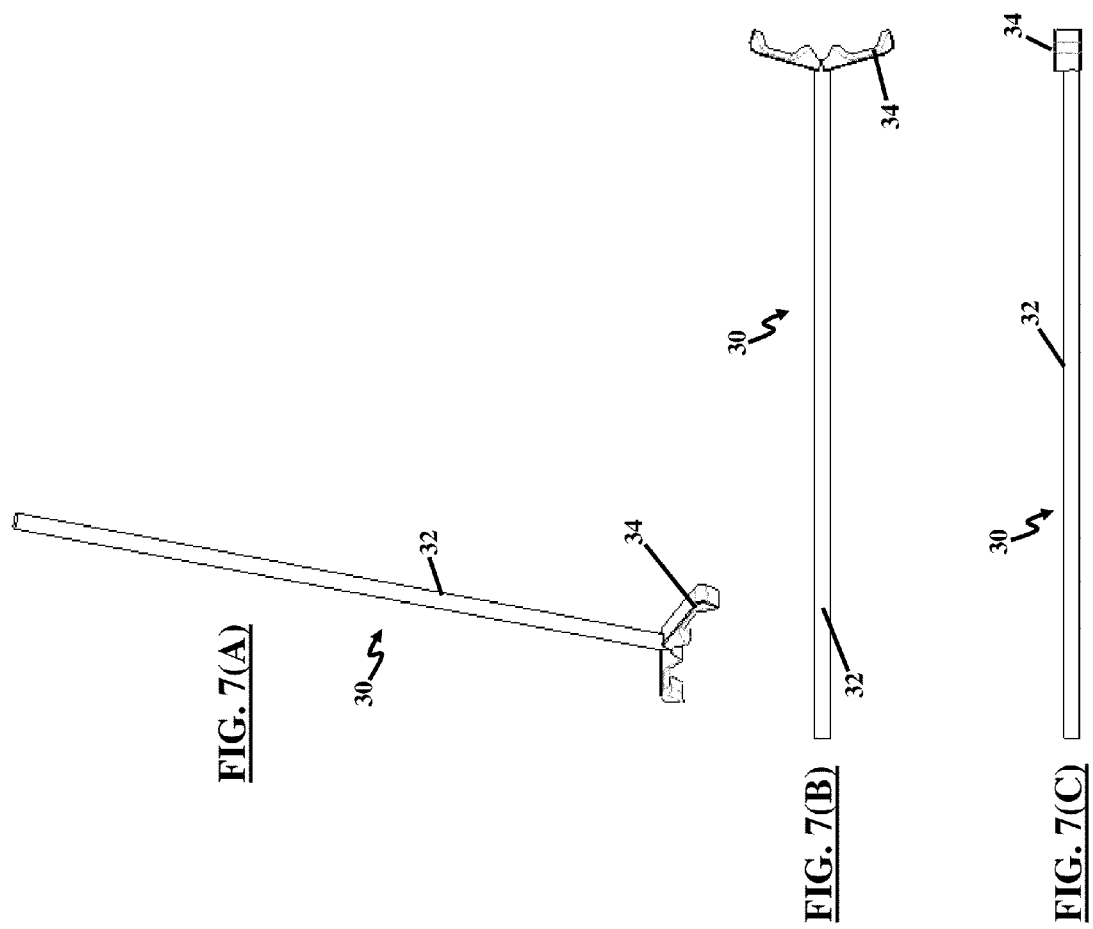

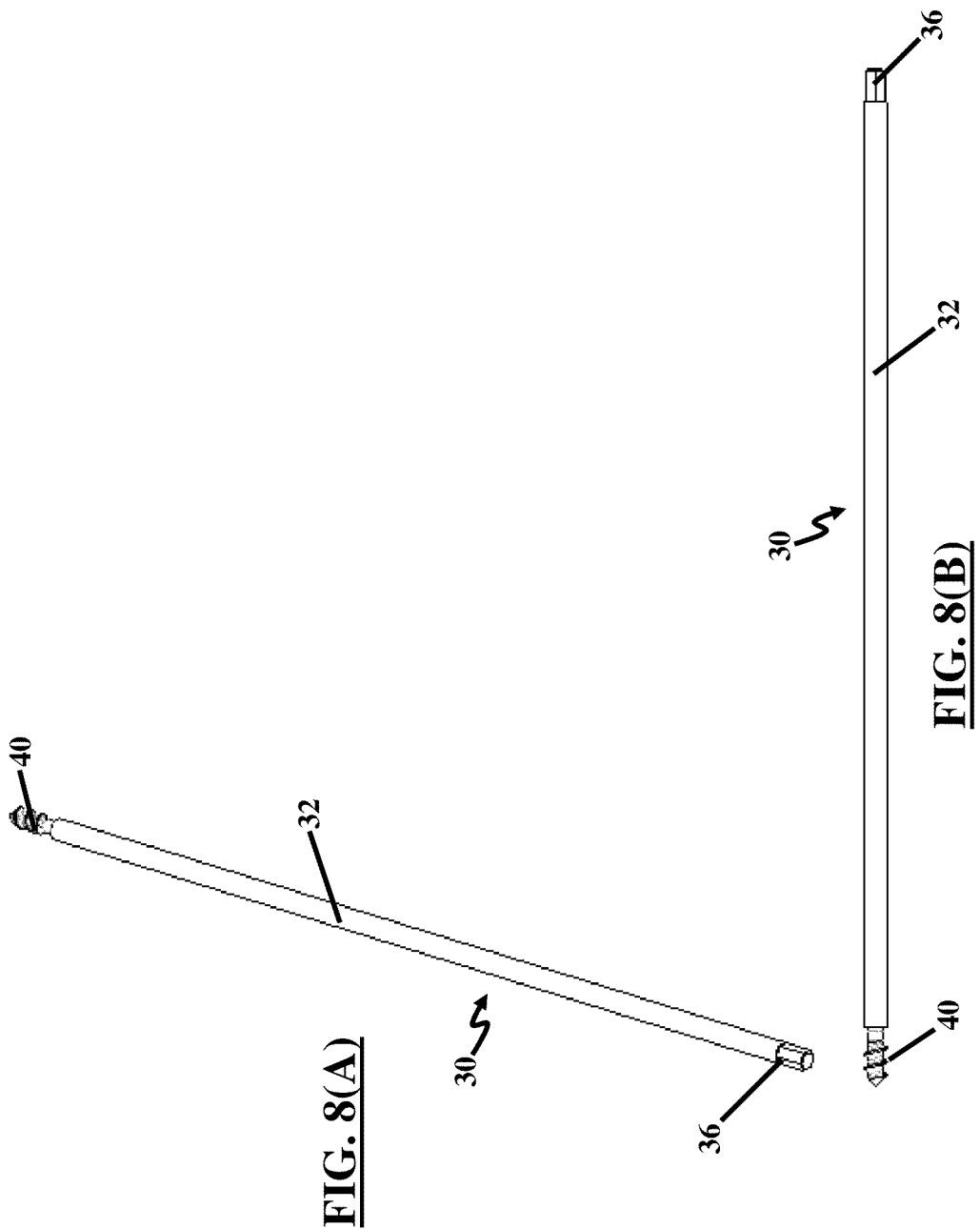

PERCUTANEOUS TUBE ASSEMBLY

BACKGROUND

1. Technical Field

The embodiments herein generally relate to surgical instruments, and, more particularly, to a percutaneous tube used during minimally invasive surgical procedures.

2. Description of the Related Art

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods. For example, a conventional percutaneous tube employed during minimally invasive surgical procedures often require temporary placement of auxiliary attachments during the procedure to be located in a position that obstructs the view of the surgeon or to be in an unstable position. These shortcomings to convention minimally invasive surgical instruments frequently raise the risk of additional morbidity to a patient undergoing a minimally invasive surgical procedure.

SUMMARY

In view of the foregoing, an embodiment herein provides a system for performing minimally invasive surgery, the system comprising a percutaneous tube comprising a translucent main body; an external attachment fixture attached to the main body; an access channel longitudinally bored through the main body; an internal attachment channel longitudinally bored through the main body, wherein the internal attachment channel comprises a partially smooth inner surface adjacent to a partially rough inner surface; and an internal attachment, mating with the internal attachment channel.

In such a system, the external attachment fixture may mate with an external attachment. Moreover, the external attachment fixture may be offset from the main body of the percutaneous tube by an angle providing unobstructed access to the access channel as the external attachment is coupled to the external attachment fixture. In addition, the main body of the percutaneous tube may comprise an access slot cut through the main body. Additionally, the main body of the percutaneous tube may comprise an upper inner smooth surface and a lower inner rough surface.

Furthermore, in such a system, the lower inner rough surface may increase the intensity of light directed into the percutaneous tube compared with the upper inner smooth surface. Moreover, the internal attachment may comprise an internal attachment fixture. In addition, the internal attachment fixture may comprise a clamp-like device. Additionally, the clamp-like device may close in response to a linear pulling force applied to the internal attachment. Furthermore, the clamp-like device may open in response to linear pushing force applied to the internal attachment. Moreover, the internal attachment fixture may comprise at least one of a pin, a screw, and a hook. In addition, the internal attachment may comprise a threaded portion that mates with the internal attachment fixture. Additionally, the internal attachment may comprise a socket-like top portion.

Another embodiment herein provides a percutaneous tube apparatus comprising a translucent main body; an external attachment fixture attached to the main body; an access channel longitudinally bored through the main body; and an internal attachment channel longitudinally bored through the main body, wherein the internal attachment channel comprises a partially smooth inner surface adjacent to a partially rough inner surface.

With such an apparatus, the main body may comprise a notch and the notch comprises a reflective patch on an interior surface of the notch. Moreover, the external attachment fixture may be adapted to mate with an external attachment. In addition, the external attachment may comprise a light source. Furthermore, the main body of the percutaneous tube may further comprise an upper inner smooth surface and a lower inner rough surface. Additionally, the lower inner rough surface increases the intensity of light directed into the main body compared with the upper inner smooth surface.

Another embodiment herein further provides a system for performing minimally invasive surgery, the system comprising a percutaneous tube comprising a translucent main body; an external attachment fixture coupled to a first end of the main body and coupled at an acute angle from the main body; an access slot partially cut longitudinally through the main body, wherein the access slot is longitudinally cut from a second end of the main body to a point on the main body between the second end and the first end, and wherein the second end is positioned opposite to the first end; an access channel longitudinally bored through the main body; an internal attachment channel longitudinally bored through the main body, wherein the internal attachment channel comprises a partially smooth inner surface adjacent to a partially rough inner surface, wherein the partially smooth inner surface begins at the first end and the partially rough inner surface terminates at the second end; and an internal attachment mating with the internal attachment channel, wherein the internal attachment comprises a top portion that comprises a socket and a bottom portion that comprises at least one of a clamp attachment, a pin attachment, and a screw attachment.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1(A) illustrates a schematic diagram of a percutaneous tube assembly according to an embodiment herein;

FIG. 3(A) illustrates a disassembled view of a percutaneous tube assembly according to an embodiment herein;

FIGS. 3(B) and 3(C) illustrate alternate views of a percutaneous tube assembly according to an embodiment herein;

FIGS. 4(A) through 4(C) illustrate a schematic diagram of a percutaneous tube assembly with a internal attachment extended according to an embodiment herein;

FIGS. 5(A) through 5(C) illustrate a schematic diagram of a percutaneous tube assembly with a internal attachment retracted according to an embodiment herein;

FIGS. 6(A) through 6(C) illustrate a schematic diagram of a percutaneous tube according to an embodiment herein;

FIGS. 7(A) through 7(C) illustrate a schematic diagram of an internal attachment with a clamp fixture according to an embodiment herein; and FIGS. 8(A) through 8(B) illustrate a schematic diagram of an internal attachment according to an embodiment herein.

DETAILED DESCRIPTION OF PREFERRED EMBODIMENTS

Figure 1B:
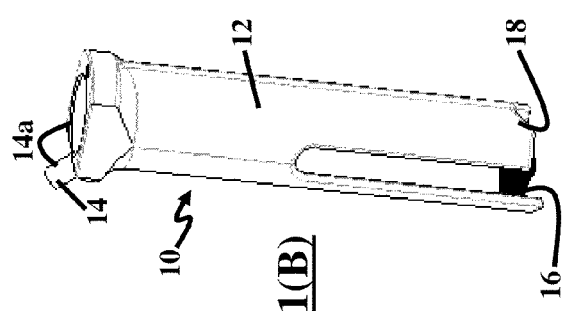
FIG. 1(B) illustrates a schematic diagram of a percutaneous tube according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned above, there remains a need for a novel percutaneous tube for use during minimally invasive surgical procedures that allows auxiliary instruments (e.g., internal and external attachments) to be securely coupled to the novel percutaneous tube and provide an unobstructed view of critical areas during surgery. The embodiments herein provide a percutaneous tube assembly with an internal fixation device embedded within the length of the percutaneous tube to allow secured attachment of the fixation device and unobstructed viewing of crucial areas during the minimally invasive surgical procedure. Referring now to the drawings, and more particularly to FIGS. 1(A) through 8(B), there are shown preferred embodiments of the invention.

FIGS. 1(A) and 1(B) illustrate a schematic diagram of a percutaneous tube assembly 1 according to an embodiment herein. As shown, percutaneous tube assembly 1 includes percutaneous tube 10, which includes a translucent main body 12, external attachment fixture 14, access slot 16, and notch 18. While not shown in FIG. 1(A), external attachment fixture 14 is configured to accept external attachments. External attachment fixture 14 is offset by angle 14a, where angle 14a is sufficient to prevent external attachments from obscuring the view of a surgeon when attached to external attachment fixture 14. Access slot 16 provides access to interior anatomical structures of a bodily cavity during a minimally invasive surgical procedure and allows manipulation of surgical implants during the minimally invasive surgery. For example, access slot 16 may be used as a passageway for inserting a rod (not shown) during a minimally invasive surgical procedure for spinal applications. Notch 18 provides a counter-shape to percutaneous tube assembly 1. For example, notch 18 may prevent percutaneous tube assembly 1 from being blocked by interior anatomical structures of a bodily cavity during a minimally invasive surgical procedure. Percutaneous tube assembly 1 also includes internal attachment 30. While not shown in FIGS. 1(A) and 1(B), internal attachment 30 may include a clamp attachment, a pin attachment, a screw attachment, a hook attachment or any other similarly useful attachments that may be used during a minimally invasive surgical procedure.

Figure 2:
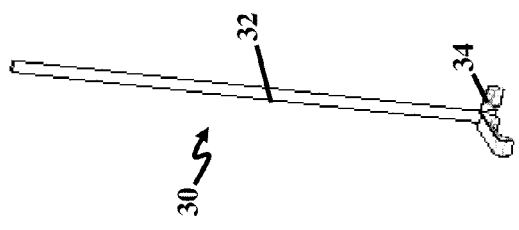
FIG. 2 illustrates a schematic diagram of an internal attachment according to an embodiment herein.

FIG. 2, with reference to FIGS. 1(A) and 1(B), FIG. 3(A), and FIGS. 8(A) and 8(B), illustrates a perspective view of an internal fixation device 30 according to an embodiment herein. The internal attachment 30 includes main body 32 and clamp attachment 34. While clamp attachment 34 is shown in FIG. 2(B) coupled to main body 32, internal attachment 30 is not limited to clamp attachment 34 and may include a pin attachment (e.g., pin attachment 38, shown in FIG. 3(A)), a screw attachment (e.g., screw attachment 40, shown in FIGS. 8(A) and 8(B)), a hook attachment or any other device appropriate during minimally invasive surgical procedures.

FIG. 3(A), with reference to FIGS. 1 through 2(B), illustrates a disassembled view of a percutaneous tube assembly 1 according to an embodiment herein. In addition, FIGS. 3(B) and 3(C), with reference to FIGS. 1 through 3(A), illustrate alternate views of a percutaneous tube assembly 1 according to an embodiment herein. Percutaneous tube 10 includes main body 12, external attachment fixture 14, access slot 16, and notch 18, as shown previously, as well as an access channel 20, and an internal attachment channel 22. Both access channel 20 and internal attachment channel 22 are channels bored through main body 12. In addition, internal attachment 30 is shown with a main body 32 and pin attachment 38. Main body 32 is configured to loosely mate with internal attachment channel 22. In FIG. 3(C), which is an A-A cross-section from FIG. 3(B), internal attachment channel 22 with main body 32 of internal attachment 30 is shown in percutaneous tube assembly 1.

FIGS. 4(A) through 4(C), with reference to FIGS. 1(A) through 3(C), illustrate a schematic diagram of a percutaneous tube assembly 1 with an internal attachment 30 extended according to an embodiment herein. Additionally, FIGS. 5(A) through 5(C), with reference to FIGS. 1(A) through 4(C), illustrate a schematic diagram of a percutaneous tube assembly 1 with an internal attachment fixture 30 retracted according to an embodiment herein. As shown previously, percutaneous tube 10 includes internal attachment channel 22 (not shown in FIGS. 4(A) through 5(C), but shown in FIG. 3(C)) that accepts internal attachment 30. As shown in FIGS. 4(A) through 5(C), internal attachment 30 may include a clamp attachment 34. While clamp attachment 34 is shown in FIGS. 4(A) through 5(C), internal attachment 30 is not limited thereto and may include a pin attachment (e.g., pin attachment 38, shown in FIG. 3(A)) or a hook attachment. In addition, internal attachment 30 may permit mechanical manipulation of clamp attachment 34 without removal from internal attachment channel 22. For example, in FIGS. 4(A) through 4(C), clamp attachment 34 is a clamp-like device with each clamp-like protrusion coupled to a spring-like device and the clamp-liked protrusions are fully extended. In FIGS. 5(A) through 5(C), however, the clamp-like protrusion of clamp attachment 34 are partially retracted because main body 12 is compressing each clamp-like protrusion causing the spring-like devices to compress and retract clamp attachment 34. Percutaneous tube assembly 1 may translate from the configuration shown in FIGS. 4(A) through 4(C) to the configuration shown in FIGS. 5(A) through 5(C) when a force (e.g., a pulling force or a pushing force) is applied to a top portion 36 of internal attachment 30, which translates through internal attachment channel 22 to effectuate the clamping mechanism (e.g., through the spring-like devices coupled to the clamp-like protrusions of clamp attachment 34) shown in FIGS. 4(A) through 5(C).

FIGS. 6(A) through 6(C), with reference to FIGS. 1(A) through 5(C), illustrate an isolated view of a percutaneous tube 10 according to an embodiment herein. In the views shown, percutaneous tube 10 includes main body 12, external attachment fixture 14, angle 14a, access slot 16, notch 18, access channel 20, internal attachment channel 22, upper inner smooth surface 24 and lower inner rough surface 26. While not shown, external attachment fixture 14 is embodied as a universal fixture that accepts a variety of different external attachments. For example, a light source (e.g., a lamp) (not shown) may be attached to external attachment fixture 14 to provide light while percutaneous tube 10 is in use during surgery. In addition, external attachment 14 is offset from main body 12 by angle 14a to allow an external attachment to be transfixed to external attachment fixture 14 and continue providing unobstructed access to access channel 20. Percutaneous tube 10 also includes an optional upper inner smooth surface 24 and an optional lower inner rough surface 26. Generally, light reflected on the smooth surface 24 creates specular reflection such that the reflected light rays are all parallel to each other causing a generally uniform light reflection on the smooth surface 24. Whereas, light reflected on the rough surface 26 creates diffuse reflection such that the reflected light rays travel in random directions causing an enhanced visibility on the rough surface 26, which increases illumination towards the notch end 18 of the percutaneous tube 10, where increased/enhanced light/visibility is desired during surgery.

FIGS. 7(A) through 7(C), with reference to FIGS. 1(A) through 6(C), illustrate a schematic diagram of an internal attachment 30 with a clamp attachment 34 according to an embodiment herein. In addition, FIGS. 8(A) through 8(B), with reference to FIGS. 1(A) through 7(C), illustrate a schematic diagram of an internal attachment 30 with a pin attachment 38 according to an embodiment herein. In the views shown, internal attachment 30 includes main body 32 and either clamp attachment 34 (shown in FIGS. 7(A) through 7(C)), pin attachment 36 (shown in FIG. 3(A)) or a screw attachment 40 (shown in FIGS. 8(A) and 8(B)). In addition, main body 32 includes a top portion 36, which is the portion of internal attachment 30 that protrudes above percutaneous tube 10 and permits manipulation during a minimally invasive surgical procedure (e.g., a pulling force or a pushing force may be applied to top portion 36). As shown, internal attachment 30 may include a clamp attachment 34 (as shown in FIGS. 7(A) through 7(C)), or a screw attachment 40 (as shown in FIGS. 8(A) and 8(B)), but may also include a pin attachment (shown in FIG. 3(A), a hook attachment (not shown) or any other similarly attachment useful during a minimally invasive surgical procedure. While top portion 36 is shown in FIGS. 8(A) through 8(B) as a polygonal socket, top portion 36 is not limited to such a configuration. In addition, as discussed above, top portion 36 may provide mechanical assistance in manipulating internal attachment fixture 32 when internal attachment 30 is secured within internal attachment channel 22 (e.g., as shown in FIG. 3(C)).

The embodiments herein provide a percutaneous tube assembly (e.g., percutaneous tube assembly 1) with an internal fixation device (e.g., internal attachment 30) embedded within the length of the percutaneous tube (e.g., through internal attachment channel 22) to allow secured attachment of the fixation device (e.g. internal attachment 30) and unobstructed viewing of crucial areas during the minimally invasive surgical procedure. Since a sturdy and unobstructed access to the surgical location is easily achievable using such a percutaneous tube assembly (e.g., percutaneous tube assembly 1), the usage of cannulated implant may be avoided. For example, instead of using a cannulated pedicle screw system, a non-cannulated pedicle screw system would be available during a minimally invasive surgical procedure.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for performing minimally invasive surgery, said system comprising:
   a percutaneous tube comprising:
      a translucent main body;
      an external attachment fixture attached to said main body;
      an access channel longitudinally bored through said main body;
      an internal attachment channel longitudinally bored through said main body, wherein said internal attachment channel comprises a partially smooth inner surface adjacent to a partially rough inner surface; and
   an internal attachment mating with said internal attachment channel, wherein said internal attachment comprises an internal attachment fixture, and wherein said internal attachment comprises a threaded portion that mates with said internal attachment fixture.

2. The system of claim 1, wherein said external attachment fixture mates with an external attachment.

3. The system of claim 2, wherein said external attachment fixture is offset from said main body of said percutaneous tube by an angle providing unobstructed access to said access channel as said external attachment is coupled to said external attachment fixture.

4. The system of claim 1, wherein said main body of said percutaneous tube comprises an access slot cut through said main body.

5. The system of claim 1, wherein said main body of said percutaneous tube comprises an upper inner smooth surface and a lower inner rough surface.

6. The system of claim 5, wherein said lower inner rough surface increases the intensity of light directed into said percutaneous tube compared with said upper inner smooth surface.

7. The system of claim 1, wherein said internal attachment fixture comprises a clamp-like device.

8. The system of claim 7, wherein said clamp-like device closes in response to a linear pulling force applied to said internal attachment.

9. The system of claim 7, wherein said clamp-like device opens in response to linear pushing force applied to said internal attachment.

10. The system of claim 1, wherein said internal attachment fixture comprises at least one of a pin, a screw, and a hook.

11. The system of claim 1, wherein said internal attachment comprises a top portion comprising a socket.

12. A percutaneous tube apparatus comprising:
a translucent main body;
an external attachment fixture attached to said main body;
an access channel longitudinally bored through said main body;
an internal attachment channel longitudinally bored through said main body, wherein said internal attachment channel comprises a partially smooth inner surface adjacent to a partially rough inner surface; and
an internal attachment mating with said internal attachment channel, wherein said internal attachment comprises an internal attachment fixture, and wherein said internal attachment comprises a threaded portion that mates with said internal attachment fixture.

13. The percutaneous tube apparatus of claim 12, wherein said main body comprises a notch and said notch comprises a reflective patch on an interior surface of said notch.

14. The percutaneous tube apparatus of claim 13, wherein said external attachment fixture is adapted to mate with an external attachment.

15. The percutaneous tube apparatus of claim 14, wherein said external attachment comprises a light source.

16. The percutaneous tube apparatus of claim 15, wherein said main body of said percutaneous tube further comprises an upper inner smooth surface and a lower inner rough surface.

17. The percutaneous tube apparatus of claim 13, wherein said lower inner rough surface increases the intensity of light directed into said main body compared with said upper inner smooth surface.

18. A system for performing minimally invasive surgery, said system comprising:
a percutaneous tube comprising:
a translucent main body;
an external attachment fixture coupled to a first end of said main body and coupled at an acute angle from said main body;
an access slot partially cut longitudinally through said main body, wherein said access slot is longitudinally cut from a second end of said main body to a point on said main body between said second end and said first end, and wherein said second end is positioned opposite to said first end;
an access channel longitudinally bored through said main body;
an internal attachment channel longitudinally bored through said main body, wherein said internal attachment channel comprises a partially smooth inner surface adjacent to a partially rough inner surface, wherein said partially smooth inner surface begins at said first end and said partially rough inner surface terminates at said second end; and
an internal attachment mating with said internal attachment channel, wherein said internal attachment comprises a top portion that comprises a socket and a bottom portion that comprises at least one of a clamp attachment, a pin attachment, and a screw attachment, wherein said internal attachment comprises an internal attachment fixture, and wherein said internal attachment comprises a threaded portion that mates with said internal attachment fixture.

19. The system of claim 18, wherein said partially rough inner surface increases the intensity of light directed into said main body compared with said partially smooth inner surface.

20. The system of claim 18, wherein said external attachment fixture mates with an external attachment.

\* \* \* \* \*